(12) United States Patent
Godoy

(10) Patent No.: US 9,132,037 B2
(45) Date of Patent: Sep. 15, 2015

(54) DIVING MASK

(71) Applicant: Carlos Alberto Godoy, Genoa (IT)

(72) Inventor: Carlos Alberto Godoy, Genoa (IT)

(73) Assignee: Cressi-Sub S.P.A., Genoa (IT)

( * ) Notice: Subject to any disclaimer, the term of this patent is extended or adjusted under 35 U.S.C. 154(b) by 196 days.

(21) Appl. No.: 13/922,414

(22) Filed: Jun. 20, 2013

(65) Prior Publication Data

US 2014/0013494 A1 Jan. 16, 2014

(30) Foreign Application Priority Data

Jul. 13, 2012 (IT) .............................. MI2012A1228

(51) Int. Cl.
*B63C 11/12* (2006.01)
*A61F 9/02* (2006.01)

(52) U.S. Cl.
CPC .. *A61F 9/02* (2013.01); *B63C 11/12* (2013.01)

(58) Field of Classification Search
CPC .. A63B 33/02; A63B 33/00; A63B 2033/004; A63B 71/10; A63B 2208/03; A63B 2208/12; A63B 2225/605; A61F 9/027; A61F 9/029; A61F 9/025; A61F 9/02; A61F 9/026; A61F 9/06; B63C 11/12; B63C 2011/128
USPC ................................ 2/426–430, 452; 351/43
See application file for complete search history.

(56) References Cited

U.S. PATENT DOCUMENTS

| | | | | |
|---|---|---|---|---|
| 5,479,917 | A * | 1/1996 | Hsieh | 128/200.29 |
| 5,819,321 | A * | 10/1998 | Wang | 2/428 |
| 6,192,523 | B1 * | 2/2001 | Pan | 2/428 |
| 6,272,693 | B1 * | 8/2001 | Godoy | 2/430 |
| 7,181,778 | B1 * | 2/2007 | Garraffa et al. | 2/428 |
| 7,305,719 | B2 * | 12/2007 | Pan | 2/430 |
| 7,699,462 | B2 * | 4/2010 | Godoy | 351/43 |
| 8,065,752 | B2 * | 11/2011 | Kuroda | 2/428 |
| 2005/0128426 | A1 * | 6/2005 | Shiue | 351/43 |
| 2006/0227285 | A1 * | 10/2006 | Huang | 351/43 |
| 2012/0246810 | A1 * | 10/2012 | Chiang | 2/428 |

* cited by examiner

*Primary Examiner* — Andrew W Collins
(74) *Attorney, Agent, or Firm* — Blank Rome LLP

(57) ABSTRACT

A diving mask including at least one lens, a facepiece made of a soft and elastically yielding material, provided with at least a front positioning opening that positions the at least one lens, and a rear profiled element that rests on a user's face. Also included is a rigid frame that includes a first frame element and a second frame element anterior to the first frame element, fixed to one another such as to guarantee a seal between the facepiece and the lens. The front positioning opening of the facepiece can exhibit, along a perimeter edge thereof, a hollow positioning flange for the first frame element, the hollow positioning flange extending from an internal side of, and at least partially posteriorly to, the front positioning opening of the facepiece.

9 Claims, 4 Drawing Sheets

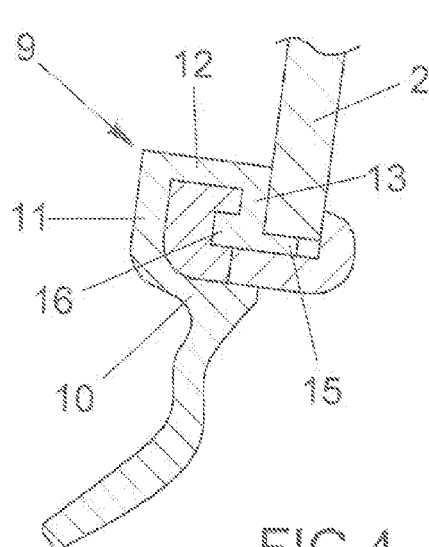
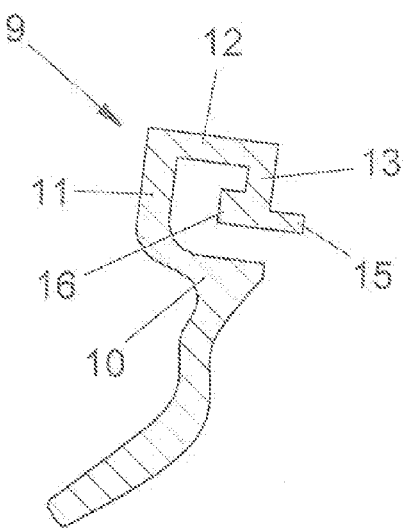
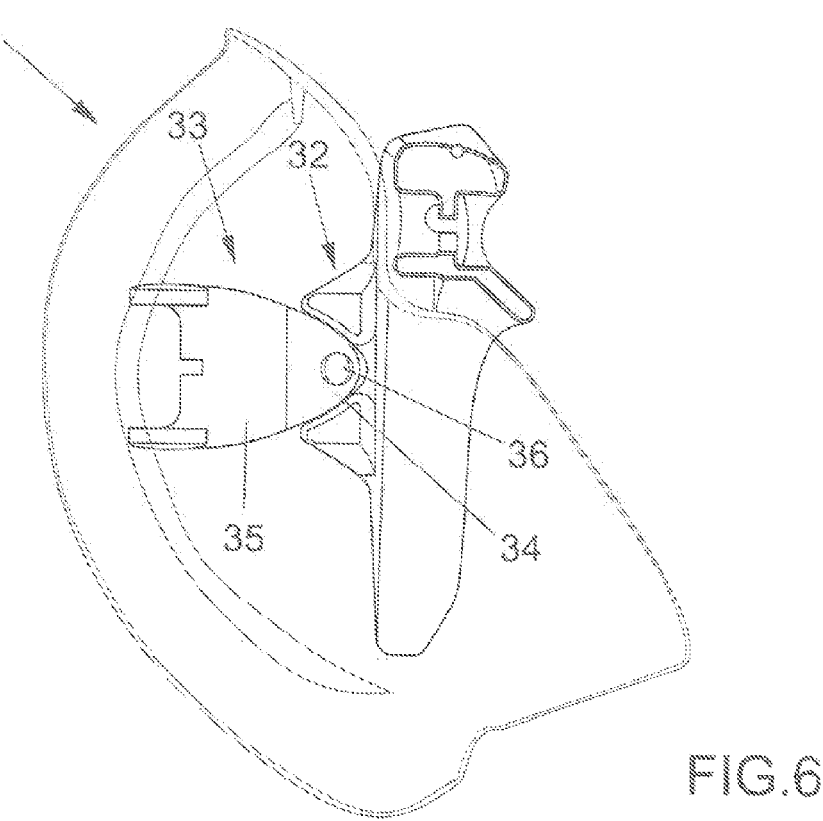

DIVING MASK

RELATED APPLICATIONS

This application claims benefit of priority under 35 USC §119 of Italy Patent Application No. MI2012A 001228, filed Jul. 13, 2012, entitled "A Diving Mask," which application is incorporated herein by reference.

FIELD OF THE INVENTION

The present invention relates to a diving mask; and more particularly to diving masks that reduce an internal space to a minimum.

BACKGROUND OF THE INVENTION

Underwater diving masks are made up of a pair of lenses (or a single lens) supported by a rigid frame about which edge a part known as a facepiece is fixed, which facepiece is formed by a sort of casing made of a soft and elastically-yielding material, provided with openings for the lenses and the rear profile of which is sealedly applied to the face of the diver.

The rigid frame ensures the seal of the lenses and the rigidity of the mask.

The rear profile of the facepiece, which is to be applied to the diver's face, is shaped such as to be complementary as much as possible to the forehead, cheeks and lower part of the user's face.

In general the facepiece provides a projection able to receive the user's nose and inferiorly terminates below the nose, thus leaving the diver's mouth free for a snorkel, if one is being used.

The term "lens" is understood to mean a transparent membrane, generally flat, made of glass or another suitable material, which only in particular cases is effectively constituted by graduated lenses adapted to correcting defects in the user's sight.

The locking of the perimeter edge of the front openings of the facepiece about the lenses of the mask is generally realised in various known ways, and determines the formation of an open internal space of the mask delimited by the internal surface of the lenses and the part of the internal surface of the facepiece which encounters the internal surface of the lenses. This internal open space is closed by the face of the user wearing the mask.

In the locking closure known as "radial", the perimeter edge of the front openings of the facepiece includes a groove facing towards the outside of the front openings in which the edge of the lenses is inserted, and the rigid frame is constituted by a single piece which locks with a force that acts in the plane of the lenses with the direction of the force facing towards the centre thereof.

In the locking closure known as "axial", the perimeter edge of the front openings of the facepiece includes a flange facing towards the outside of the front openings, and the rigid frame is in general made up by two elements between which both the flange and the edge of the lenses are locked.

One of the drawbacks of the known-type diving masks consists in the fact that all the component elements ensuring the seal of the lenses and the rigidity of the mask determine a quite large internal space in the mask.

When the diver is swimming on the surface, this closed internal space is at atmospheric pressure. When the diver plunges below the surface, the pressure of such internal space must be compensated.

If the diver is provided with cylinders, the compensation is achieved by means of the air contained in the lungs which the diver can however top up with the gas contained in the cylinders. When on the other hand the diver dives in apnea, the compensation of the pressure in the internal space is done using the oxygen in his or her lungs but without any possibility of a top-up.

This leads to the need to reduce this internal space of divers' masks to a minimum.

To remedy this drawback it has been proposed to suitably position a filler material in the internal space of the mask. This expedient however adds one more element to the components of the mask, and thus increases the production cost and reduces the visual field of the user.

Alternatively the seal between the facepiece and the lenses can be ensured by gluing and overmoulding the edge of the openings in the facepiece to the lenses. In this case the rigidity of the mask is ensured by the glued or overmoulded frame. This solution enormously complicates the production process, which is longer and more expensive.

A further drawback of known-type diving masks consists in the fact that the solution used for the locking often makes the profile of the mask poorly hydro-dynamic in the connecting zone of the frame with the facepiece, with in particular the formation of large recesses between the frame and the facepiece which apart from constituting possible points of catching or dirt buildup, when the user swims can generate a turbulence in the water about the lenses, with a consequent deterioration of the sharpness of the visual field.

SUMMARY OF THE INVENTION

Embodiments of the present invention will be seen variously to:

realize a diving mask which obviates the technical drawbacks of the prior art;

realize a diving mask which enables optimizing a duration of immersion by limiting the compensation of the air pressure which the diver has to perform for immersion without penalizing the size of the visual field;

realize a diving mask which exhibits a hydrodynamic profile in the connecting zone of the frame with the facepiece; and provide a diving mask that can be realized in a simple and economical way.

The above is attained by realizing a diving mask of a type comprising at least a lens, a facepiece made of a soft and elastically yielding material, provided with at least a front opening for positioning said at least a lens and a rear profiled element for resting on a user's face, and a rigid frame comprising a first frame element and a second frame element anterior to the first frame element, fixed to one another such as to guarantee a seal between said facepiece and said at least a lens, characterised in that said at least a front opening of the facepiece exhibits, along a perimeter edge thereof, a hollow positioning flange for at least said first frame element, said hollow flange extending from the internal side and at least partially posteriorly to said at least a front opening of the facepiece, said hollow flange further having a transversal section substantially in an open polygonal spiral shape.

This special construction for the hollow positioning flange advantageously allows a dismountable mechanism connection as opposite to permanent mechanical connection provided by a known technique involving gluing and/or moulding.

Other characteristics of the present invention are further defined in the following claims.

BRIEF DESCRIPTION OF THE DRAWINGS

Further characteristics and advantages of the invention will emerge more fully from the description of a preferred but not exclusive embodiment of the diving mask according to the invention, illustrated by way of non-limiting example in the accompanying figures, in which:

FIG. 4 is an enlarged-scale detail of FIG. 3 above;

FIG. 5 reproduces FIG. 4, limited to the facepiece parts; and

FIG. 6 is a variant of the attachment of the buckle to the frame of the mask.

DETAILED DESCRIPTION OF THE ILLUSTRATED EMBODIMENTS

Figure 1:
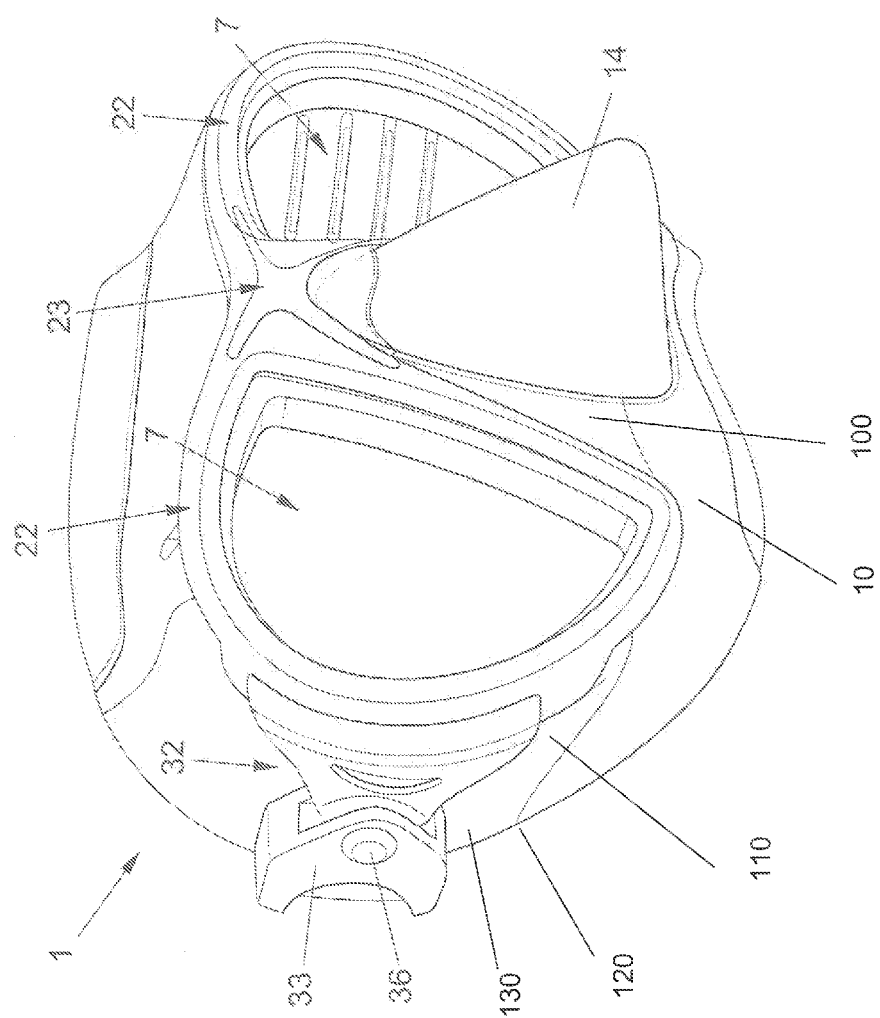
FIG. 1 is a perspective view of a diving mask of the invention.
Figure 2:
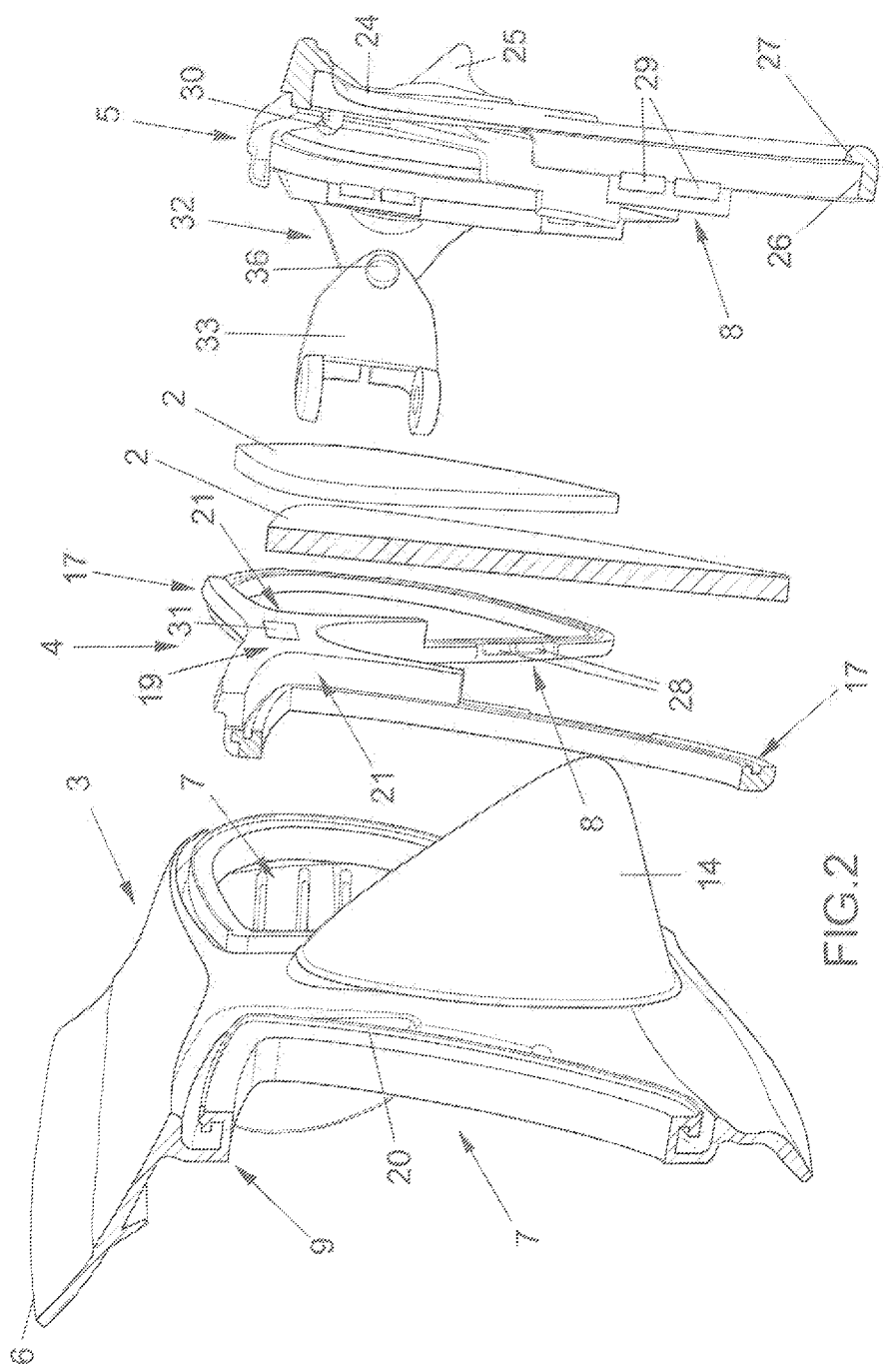
FIG. 2 is an exploded sectional view of the mask of the invention.
Figure 3:
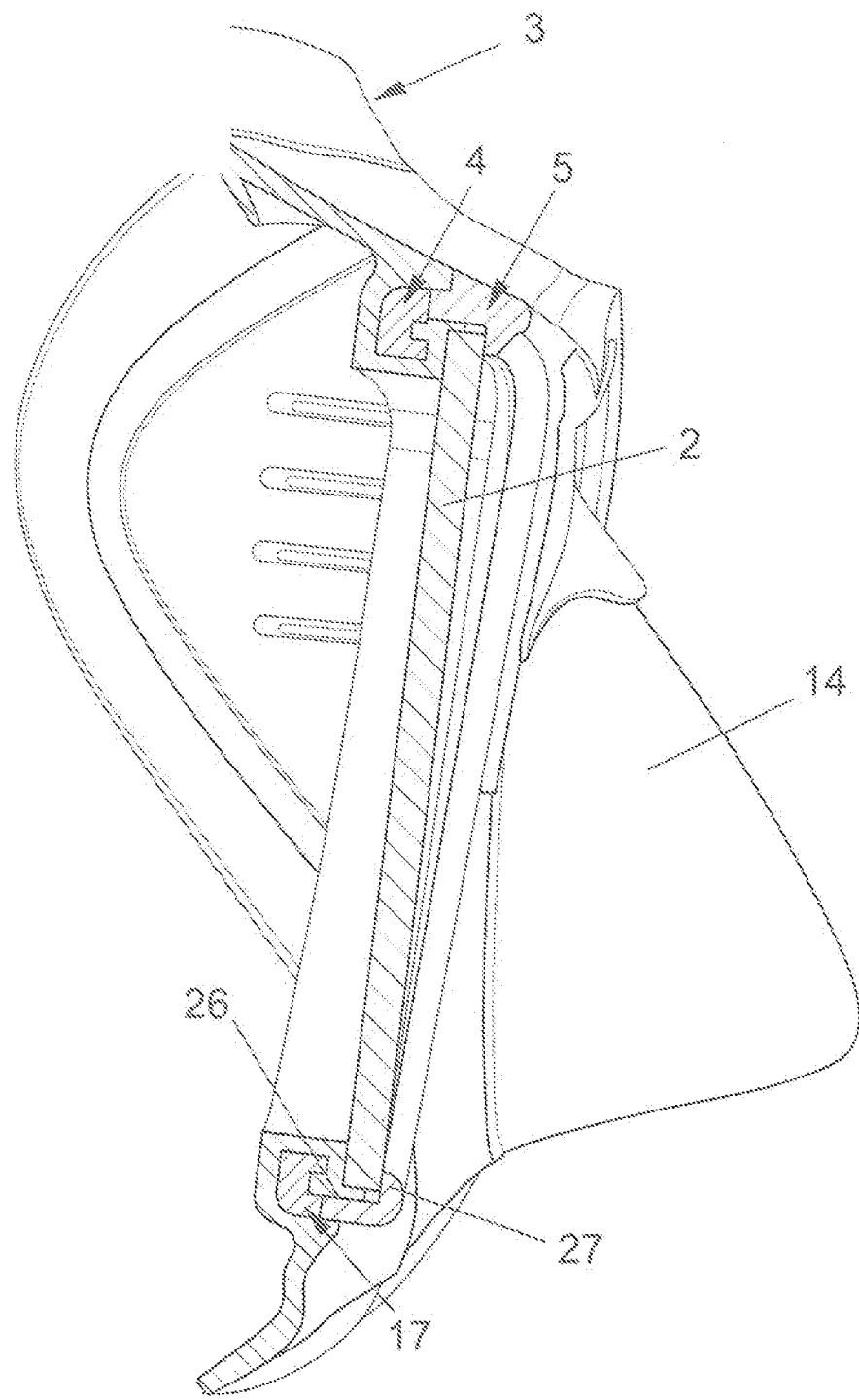
FIG. 3 is a view of the assembled mask, sectioned along a plane that is perpendicular to the lying plane of the lenses and passing through one them.

With reference to the above-cited figures, a diving mask is illustrated, denoted in its entirety by reference number 1.

The mask 1 comprises at least a lens 2, and in particular in the illustrated solution a right lens 2 and a left lens 2, a facepiece 3 made of a soft and elastically yielding material, and a rigid frame, in particular made of plastic, comprising a first frame element 4 and a second frame element 5 anterior of the first frame element 4. The facepiece 3 exhibits a rear profiled element 6 for resting on the user's face and frontally a corresponding positioning opening 7 for each lens 2.

The first frame element 4 and the second frame element 5 are reciprocally connected by fixing means 8 which are able to guarantee seal between the facepiece 3 and the lenses 2.

One of the principle characteristics of the mask consists in the fact that each opening 7 of the facepiece 3 exhibits, along the perimeter edge thereof, a hollow positioning flange 9 at least for the first element of the frame 4.

The hollow flange 9 extends from the internal side and at least partially posteriorly to the opening 7.

Each hollow flange 9 is configured and arranged such as to limit, with the volume thereof, the internal space of the mask closed between the user's face, the internal surface of the facepiece 3 and the internal surface of each lens 2.

The flange 9 has in particular a transversal section substantially in the shape of an open polygonal spiral, and more precisely comprises a first wall 10 which develops laterally and perpendicularly to the lens 2, a second wall 11 which extends perpendicularly to the first wall 10, parallel to and below the lens 2, a third wall 12 which extends perpendicularly to the second wall 11, perpendicularly and below the lens 2, and a fourth wall 13 for perimeter support of the lens 2, which extends perpendicularly to the third wall 12 and anteriorly of the second wall 11.

The first wall 10, along 100 (a tract of a perimeter edge of the opening 7 delimiting the projection 14 of the facepiece 3 in order to accommodate the user's nose), develops partly anteriorly and partly posteriorly of the perimeter edge of the opening 7 while in the remaining tract 110 of the perimeter edge of the opening 7 the depth of penetration of the first wall 10 on the rear side of the opening 7 decreases gradually up to zero at point 120 at the temple zone 130 of the facepiece 3.

The flange 9 further comprises, perpendicularly to the fourth wall 13, a fifth wall 15 which circumscribes the lens 2 such as to laterally contain it.

The flange 9 lastly comprises a sixth wall 16 which extends from the fourth wall 13 symmetrically to the fifth wall 15.

The first frame element 4 comprises a right annular portion 17 positioned along the hollow flange 9 of the perimeter edge of the right front opening 7 of the facepiece 3, a left annular portion 17 positioned along the hollow flange 9 of the perimeter edge of the left front opening 7 of the facepiece 3, and a central connecting portion 19 between the right annular portion 17 and the left annular portion 17.

The central portion 19 of the first frame element 4 is arranged projectingly from the front surface of the right annular portion 17 and the left annular portion 17 of the first frame element 4 in such a way to be able to distance from the facepiece zone 3 which will house the top of the user's nose.

The central portion 19 of the first frame element 4, flattened and symmetrical with respect to the median plane of the mask longitudinally crossing the projection 14, circumscribes a tract 20 of the fifth wall 15 of the flange 9 of the perimeter edge of the right front opening of the facepiece 2 and a corresponding tract 20 of the fifth wall 15 of the flange 9 of the perimeter edge of the left front opening of the facepiece 2.

In particular, the central portion 19 of the first frame element 4 has a right angled branch 21 able to laterally contain the tract 20 of the fifth wall 15 of the right flange 9, and a left angled branch 21 able to laterally contain the tract 20 of the fifth wall 15 of the left flange 9. The annular portion 17 of the first frame element 4 exhibits a U-shaped transversal section having a conjoining and matching shape with the transversal section of the cavity of the flange 9 in which it is embedded.

The second frame element 5 substantially exhibits the same shape as the first frame element 4 on which it is superposed.

The second frame element 5 also comprises a right annular portion 22 superposed on the right annular portion 17 of the first frame element 4, a left annular portion 22 superposed on the left annular portion 17 of the first frame element 4, and a central connecting portion 23 between the right annular portion 22 and the left annular portion 22, superposed on the central portion 19 of the first frame element 4.

Each annular portion 22 exhibits a substantially L-shaped transversal section, while the connecting portion 23 exhibits a flattened zone 24 and preferably a stiffening rib 25 which develops anteriorly to the flattened zone 24. In this way the frame is centrally reinforced where it exhibits a lower resistance to flexion.

The annular portion 22 in particular exhibits a first wall 26 that is perpendicular to the lie plane of the lens 2, which rests on the first frame element 4 and laterally contains the fifth lateral wall 15 of the flange 9, and a second wall 27, parallel to the lens 2, which rests against the front surface thereof.

The fixing means lock the lens 2 axially, i.e. in a perpendicular direction to the lie plane thereof, between the front surface of the fourth wall 13 of the flange 9 and the posterior surface of the second wall 27 of the annular portion 22 of the second frame element 5.

The means for reciprocally fixing the first frame element 4 and the second frame element 5 comprise teeth 28 which can be engaged in snap seats 29.

The teeth 28 radially extend towards the outside from the perimeter edge of the right annular portion 17 and the left annular portion 17 of the first frame element 4, while the snap seats 29 are provided on the first wall 26 of the right annular portion 22 and the left annular portion 22 of the second frame element 5.

An additional fastening is preferably provided, made by engaging a tooth 30, provided on the posterior surface of the central portion 23 of the second frame element 5, in a snap seat 31 provided on the front surface of the central portion 19 of the first frame element 4.

According to the present invention the internal space of the mask is reduced by means of a suitable configuration and arrangement of each flange 9 and the two constituting parts 4, 5 of the frame which ensure the correct position 2 of the lenses 2 and the seal of the mask itself.

As can be seen from the figures, only the second wall 27 of the second frame element 5 projects anteriorly of the front surface 2 of the lenses 2, together with the projection 14 of the facepiece 3.

Each annular portion 22 of the second frame element 5 exhibits an attachment 32 to which an anchoring buckle 33 for a belt that is applicable about the user's head for retaining the mask in position is hingedly connected by means of a pin 36.

The attachment 32 is advantageously made of a soft thermoplastic rubber comoulded with the second frame element 5 in such a way as to be able to guarantee the buckle 33 an oscillation also about a perpendicular axis to the axis of the pin 36 due to the flexion of the attachment 32. In this case the buckle 33 is preferably made in a single rigid piece.

Alternatively, if the attachment 32 is made of the same material as the second frame element 5, the buckle 33 can be provided in a rigid part 34 comoulded with a soft part 35 in turn pivoted by the pin 36 to the second frame element 5 in such a way as to make the buckle 33 oscillatable both about the axis of the pin 36 and about a perpendicular axis to the axis of the pin 36 due to the torsion of the soft part 35.

The assembly of the mask is extremely simple and provides for inserting the annular portions 17 of the first frame element 4 in the corresponding flanges 9 of the facepiece 3.

Then each lens 2 is positioned, resting the perimeter edge of the fourth wall 13 of the corresponding flange 9. In this step the fifth wall 15 of the lateral containing flange 9 of the lens 2 aids centring.

Subsequently the second frame element 5 is applied, resting the second wall 27 of each annular portion 22 on the perimeter edge of the corresponding lens 2.

Finally an axial compression is applied between the first frame element 4 and the second frame element 5 in order to achieve a reciprocal snap-fit.

It should be noted that providing a hollow flange conformed with a spiral transversal section embedding the first frame element enables the facepiece to connect perfectly with the second frame element so that the hydrodynamic profile of the mask is improved, and indeed is also free of recesses which might constitute points of catching or dirt buildup.

The providing of a mechanical lock for the sealing of the lenses, with a consequent elimination of any gluing step of the lenses, makes the assembly process of the mask very simplified and enables, among other things, using a comoulded component comprising the second frame element and the attachments for the buckle, which in turns simplifies the productive process of the mask components.

The diving mask as it is conceived is susceptible to numerous modifications and variants, all falling within the scope of the inventive concept; further, all the details can be replaced with technically equivalent elements.

In practice, the materials used, as well as the dimensions, can be any according to the requirements and the state of the art.

What is claimed is:

1. A diving mask, comprising:
   at least one lens including a right lens and a left lens;
   a facepiece of elastically yielding material, the facepiece including;
      at least one front positioning opening that includes a right anterior opening and a left anterior opening, and that positions the at least one lens; and
      a rear profiled element that rests on a user's face; and
   a rigid frame including:
      a first frame element; and
      a second frame element anterior to the first frame element, where the first and the second frame elements are fixed to one another to guarantee a seal between the facepiece and the at least one lens;
   wherein the front positioning opening of the facepiece exhibits, along a perimeter edge thereof, a hollow positioning flange for at least the first frame element, the hollow positioning flange extending from an internal side of, and at least partially posteriorly to, the front positioning opening of the facepiece;
   wherein the first frame element comprises:
      a right annular portion positioned along the hollow positioning flange of the perimeter edge of the right anterior opening of the facepiece, the right annular portion positioning the right lens;
      a left annular portion positioned along the hollow positioning flange of the perimeter edge of the left anterior opening of the facepiece, the left annular portion positioning the left lens; and
      a central connecting portion between the right annular portion and the left annular portion, the central connecting portion arranged projectingly from a front surface of the right and the left annular portions; and
   wherein the hollow positioning flange has a transversal section substantially in an open polygonal spiral shape, and comprises;
      a first wall which develops laterally and perpendicularly to the right lens and the left lens;
      a second wall which extends perpendicularly from the first wall, and parallel to and below the right lens and the left lens;
      a third wall which extends perpendicularly from the second wall, and perpendicular to and below the right lens and the left lens;
      a fourth wall having a perimeter rest support for the right lens and the left lens, the fourth wall extending perpendicularly to the third wall and anteriorly to the second wall;
      a fifth wall, perpendicular to the fourth wall, wherein the fifth wall surrounds the right lens and the left lens; and
      a sixth wall, extending from the fourth wall symmetrically to the fifth wall.

2. The diving mask of claim 1, wherein the hollow positioning flange is configured to limit, with a volume thereof, a closed space between the user's face, the internal surface of the facepiece, and the internal surface of the at least one lens.

3. The diving mask of claim 1, wherein the first wall,
   along a tract of a perimeter edge of the first positioning opening that delimits a projection of the facepiece for accommodating the user's nose, develops partly anteriorly and partly posteriorly of the perimeter edge of the first positioning opening, while in a remaining tract of the perimeter edge of the first positioning opening a depth of penetration of the first wall, from the posterior side of the first positioning opening, gradually decreases until reduced to nothing.

4. The diving mask of claim 1, wherein the left and the right annular portions exhibit a U-shaped transversal section having a conjoining and matching shape to the transversal section of a cavity of the hollow positioning flange in which the left and the right annular portions are incorporated.

5. The diving mask of claim 1, wherein the central connecting portion surrounds a tract of the fifth wall of the hollow positioning flange of the perimeter edge of the right anterior opening of the facepiece, and of the hollow positioning flange of the perimeter edge of the left anterior opening of the facepiece, for lateral containing thereof.

6. The diving mask of claim 1, wherein the second frame element substantially exhibits a same shape as the first frame element on which the second frame element is superposed.

7. The diving mask of claim 6, wherein the second frame element exhibits a stiffening rib at a zone superposed on the central connecting portion of the first frame element.

8. The diving mask of claim 1, wherein the second frame element exhibits at least one attachment to which a buckle is articulatedly connected, wherein the buckled comprises a rigid part comoulded with a soft part pivoted by a pin to the second frame element.

9. The diving mask of claim 1, wherein the second frame element is comoulded with at least one attachment made of a soft material to which a buckle is articulatedly connected.

\* \* \* \* \*